United States Patent
Miller et al.

(10) Patent No.: US 8,377,713 B2
(45) Date of Patent: Feb. 19, 2013

(54) DETECTION OF EXPLOSIVES THROUGH LUMINESCENCE

(75) Inventors: Dale R Miller, Derwood, MD (US);
Sarah J Toal, Rockville, MD (US);
Russell P Watson, Montgomery Village, MD (US)

(73) Assignee: Redxdefense, LLC, Rockville, MD (US)

( * ) Notice: Subject to any disclaimer, the term of this patent is extended or adjusted under 35 U.S.C. 154(b) by 0 days.

(21) Appl. No.: 12/995,860

(22) PCT Filed: Jun. 2, 2009

(86) PCT No.: PCT/US2009/045930
§ 371 (c)(1),
(2), (4) Date: Dec. 2, 2010

(87) PCT Pub. No.: WO2010/044920
PCT Pub. Date: Apr. 22, 2010

(65) Prior Publication Data
US 2011/0081723 A1    Apr. 7, 2011

Related U.S. Application Data

(60) Provisional application No. 61/091,604, filed on Aug. 25, 2008, provisional application No. 61/129,063, filed on Jun. 2, 2008, provisional application No. 61/129,062, filed on Jun. 2, 2008.

(51) Int. Cl.
*G01N 21/76* (2006.01)

(52) U.S. Cl. .......... 436/172; 436/61; 436/110; 436/111; 436/164; 422/430

(58) Field of Classification Search .................. None
See application file for complete search history.

(56) References Cited

U.S. PATENT DOCUMENTS

| | | | |
|---|---|---|---|
| 5,480,612 A | 1/1996 | Margalit | |
| 2001/0040232 A1 | 11/2001 | Bawendi et al. | |
| 2006/0084176 A1 | 4/2006 | Almog | |
| 2006/0223076 A1 | 10/2006 | Diwu et al. | |

FOREIGN PATENT DOCUMENTS

WO    WO 2008/005096    1/2008

OTHER PUBLICATIONS

Starks, C.M., Phase-Transfer catalysis. I. Heterogeneous reactions involving anion transfer by quaternary ammonium and phosponium salts, 1971, Journal of the American Chemical Societ, vol. 93(1), pp. 195-199.*

Holmes, R. R. et al. A simple method for the direct oxidation of aromatic amines to nitroso compounds, 1960, Journal of American Chemical Society, vol. 82(13), pp. 3454-3456.*

Schulte-Ladbeck, R. et al. A field test for the detection of peroxide-based explosives, 2002, Analyst, vol. 127, pp. 1152-1154.*

* cited by examiner

*Primary Examiner* — Robert Xu
(74) *Attorney, Agent, or Firm* — Diederiks & Whitelaw, PLC

(57) ABSTRACT

A method of simultaneously detecting peroxide and nitrogen-based explosives includes the steps of applying a conversion reagent to a sample, the conversion reagent oxidizing in the presence of peroxide and inorganic nitrate explosives; applying a test reagent including a luminescent compound to the sample; exciting the luminescent compound with ultraviolet light; and simultaneously determining the presence of one or more explosives based on quenching, brightening or a shift in wavelength of the luminescence over time. Explosives may also be detected based on color changes of the sample. Optionally, phase transfer reagents, catalysts, colorimetric agents and zinc dust may be added to improve detection of explosives. Alternatively, an assay-type method may be utilized wherein a sample is added to the conversion and/or test reagents and the reagent is spotted on a substrate before exposure to ultraviolet light.

20 Claims, No Drawings

DETECTION OF EXPLOSIVES THROUGH LUMINESCENCE

CROSS-REFERENCE TO RELATED APPLICATIONS

The present application represents a National Stage application of PCT/US2009/0045930 filed Jun. 2, 2009 entitled "Detection of Explosives Through Luminescence" and claims the benefit of U.S. Provisional Patent Application Ser. No. 61/129,062 entitled "Optical Detection of Inorganic Nitrogen-Based Explosives," filed Jun. 2, 2008, and U.S. Provisional Patent Application Ser. No. 61/129,063 entitled "Detection of Peroxide-Based Explosives Through Luminescence Quenching" filed Jun. 2, 2008, and U.S. Provisional Patent Application Ser. No. 61/091,604 entitled "Detection of Explosives through Luminescence Quenching," filed Aug. 25, 2008.

BACKGROUND OF THE INVENTION

1. Field of the Invention

The present invention pertains to analyte detection and, more specifically, to the use of luminescent compounds for the detection of explosives, such as nitroaromatic-, nitramine-, nitrate-ester-, inorganic nitrate-, chlorate-, perchlorate-, bromate-, peroxide-, smokeless powder- and black-powder-based explosives.

2. Discussion of the Prior Art

Peroxide-based explosives packaged within improvised explosive devices (IEDs) are a mainstay for some terrorist groups around the world. Peroxides are highly sensitive to heat, shock, and friction, and are capable of causing substantial damage. Triacetone triperoxide (TATP) is one type of peroxide-based explosive typically used, because it may be prepared from household chemicals that are easy to obtain. Three other examples of peroxide-based explosives are hydrogen peroxide, HMTD (hexamethylene triperoxide diamine) and MEKP (methyl ethyl ketone peroxide). The primary factors affecting the growing use of peroxide-based explosives are twofold. First, techniques used to detect traditional nitrogen based high explosives such as trinitrotoluene (TNT), cyclotrimethylenetrinitramine (RDX) and pentaerythritol tetranitrate (PETN) have shown impressive advancements in recent years, which make the use of these explosives riskier for terrorists. Second, regulation, lack of availability of military grade explosives and difficulty of production of source materials create situations where traditional explosives are not practical for some terrorist groups. These two factors provide the impetus for terrorists to adapt their destructive repertoire to include peroxide-based explosives. The progression seen in the Israeli conflict from using traditional high explosive IED's to peroxide based IED's underscores the urgent need to detect this class of dangerous explosives. Moreover, it highlights the necessity for innovative solutions to terror activities, which are constantly evolving and adapting. In addition, it would be advantageous to incorporate peroxide sensing into a system which would be capable of detecting multiple classes of explosives so as to provide quick and simultaneous detection of each.

Optical sensing methods are often desired for trace explosive screening because they can be packaged into simple-to-use, low-cost devices. In contrast, conventional detection methods, such as X-ray diffraction, nuclear quadrupole resonance, ion mobility spectrometry, and gas chromatography-mass spectrometry, though highly sensitive, are expensive, difficult to maintain; susceptible to false-positives, and are not easily manufactured into low-power, portable devices.

Colorimetric techniques are also known which can detect the presence of peroxides. One such method uses acids and potassium iodide which reacts with peroxides to yield a brown color or a blue color when also in the presence of starch. Strong acids are often required to decompose organic peroxides to hydrogen peroxide, the chemical often detected by the colorimetric reactions. Portable colorimetric chemical sensing kits have the value of displaying easily interpreted optical signals with fast response times. However, there remains a demand for explosives sensors which maintain the simplicity of use and interpretation found in colorimetric kits, but with improved detection sensitivities and reduced exposure to toxic or corrosive chemicals, such as the acids used in the method mentioned above. Other desirable attributes of the sensors would be a simple one-step detection technique for peroxides which may be packaged with optical detection methods for other explosives to yield screening devices capable of detecting a wide range of explosives quickly.

Inorganic nitrates, such as uronium nitrate (commonly referred to as urea nitrate), ammonium nitrate, and potassium nitrate, are common components of industrial, military, and homemade (e.g., pipe bomb) explosives. The rapid and sensitive detection of these compounds can therefore be used to identify possible explosive threats. Because inorganic nitrates are not highly volatile, solid state sampling techniques may be favored for their detection. Colorimetric techniques are available for the rapid and simple detection of inorganic nitrates which require a series of chemical transformations. These methods, however, have a number of disadvantages, including low sensitivity, high false alarm rates, and inconvenient analysis and clean-up procedures. In addition, these methods can often expose users to large quantities of chemicals through repeated wet-chemistry style sampling steps.

The present invention provides a method whereby both trace peroxide-based explosives and trace nitrogen-based explosives may be reliably detected without the disadvantages of the prior art.

SUMMARY OF THE INVENTION

The present invention relates to a method for the simultaneous detection of multiple classes of explosives, including nitroaromatic-, nitramine-, nitrate-ester-, inorganic nitrate-, chlorate-, perchlorate-, bromate-, peroxide-, smokeless powder- and black-powder-based explosives, via use of luminescent compounds. Detection is performed in one or more steps, such that detection of each class of explosives is accomplished concurrently or in series. At least one of a conversion reagent, which oxidizes in the presence of peroxide explosives and inorganic nitrate explosives, and a phase transfer reagent is applied to a sample substrate. A test reagent including a luminescent compound is also applied to the sample substrate, and the luminescent compound excited utilizing an ultraviolet light. The quenching, brightening or a shift in wavelength of the luminescence of the compound is utilized to determine the presence of explosives. Optionally, a colorimetric reagent may be utilized, wherein a change in color indicates the presence of an explosive. Additional objects, features and advantages of the present invention will become more readily apparent from the following detailed description of preferred embodiment s of the invention.

DETAILED DESCRIPTION OF THE INVENTION

Nitroaromatics, in general, and nitroaromatic-based explosives such as TNT and Tetryl, quench the luminescence of luminescent compounds (luminophores), such as conjugated organic polymers. In nitroaromatics, the $\pi^*$ lowest unoccupied molecular orbitals (LUMOs) are of low energy due to the electron-withdrawing effect of the nitro substituent on the aromatic ring. Hence, organic molecules functionalized with nitro groups have increased electron-accepting abilities. In accordance with the present invention, luminescence quenching is monitored to effect the detection of nitroaromatic-based explosives through electron transfer luminescence quenching. Additionally, in accordance with the present invention, the oxidation of nitroaromatics is utilized to effect the detection of peroxides. Conventional high explosives, such as nitroaromatics, nitramines, and nitrate esters are detected by electron-transfer fluorescence or luminescence quenching. Other explosives are also oxidizing agents, and can be detected using fluorescent materials. For example, a conversion reagent, such as an organic amines or nitroso compound, is oxidized using hydrogen peroxide or organic peroxide explosives to cause quenching in a luminescent material. The system can be used to detect other compounds of interest, such as inorganic nitrate, chlorate-, perchlorate-, bromate-, smokeless powder- and black-powder-based explosive through luminescence quenching. One possible mechanism is the oxidation, photo-assisted or acid catalyzed, of the conversion reagent to a quencher.

Luminescent compounds are often highly conjugated chemicals and are found in a variety of chemical classes, such as aromatic hydrocarbons (e.g., 9,10-diphenylanthracene), aromatic heterocycles (e.g., 2,3-diaminonapthalene), conjugated organic polymers (e.g., polyfluorenes), and inorganic polymers (e.g., polymetalloles), to name a few. Conjugation of electrons results in a low energy $\pi^*$ lowest unoccupied molecular orbital and a low energy delocalized excited state. Delocalization of the excited state in conjugated polymers is advantageous in that exciton migration increases the frequency of quenching events with bound analytes. Conjugated compounds are often electron donors. Thus, these luminescent materials may be used for redox sensing of electron-deficient analytes, such as nitroaromatics through electron-transfer, which may results in a change in the luminescence, such as luminescence quenching.

The invention described herein is a method for detecting multiple classes of explosives simultaneously using one or more fluorescent or luminescent materials. The invention includes detecting peroxide-based explosives indirectly by using the peroxide to chemically transform a conversion reagent into a quenching species, for example, converting aromatic amines or nitrosoaromatics into electron-accepting nitroaromatics. The quenching species generated in situ are then directly detected through electron transfer luminescence quenching of the luminescence of electron donating compounds. Peroxide may also transform the conversion reagent into an ultraviolet (UV)-absorbing material, such as an azo or diazonium compound, which may then be detected against a luminescent background supplied by a luminescent reagent. It should be understood that a quenching agent for quenching of luminescence, as utilized herein, is intended to refer both to the quenching species discussed above and the UV-absorbing compounds. This method also allows an observer to distinguish between peroxide-based explosives and some potential interferents via a colorimetric technique, as some chemical analogues of peroxide-based explosives show a color change in the presence of the aromatic amine. Importantly, the colorimetric technique to identify the chemical analogues of peroxide-based explosives using aromatic amines may be used in systems not geared toward peroxide-based explosive detection, but either alone or in conjunction with other explosive detection methods.

In addition, this method may also detect inorganic nitrate explosives and others such as bromate and chlorate explosives. In particular, ammonium and urea nitrate may be detected using the conversion reagent and a detection or test reagent. The nitrate may undergo photo-assisted or acid catalyzed oxygen transfer to the conversion reagent, such as an amine. The amine compound would then be converted to a nitro compound. Aromatic amines may be particularly useful, in that the resultant product would be a nitroaromatic with high quenching efficiency of luminescent materials. It is possible that conjugated amines or alkyl amines would also be useful conversion reagents. The acid cation in the case of ammonium or uranium nitrate may also undergo acid base chemistry with an amine to make the newly protonated amine a more efficient oxidizer and hence luminescence quencher.

A first method for detection of multiple explosives in accordance with the invention will now be discussed in more detail. Advantageously, the method allows for simultaneous detection of nitroaromatic-, nitramine-, nitrate ester-, inorganic nitrate-, chlorate-, perchlorate-, bromate-, peroxide-, smokeless powder- or black powder-based explosives. Initially, a user will collect a sample from a surface to be tested utilizing a sample substrate, such as filter paper, cellulose-based paper, glass fiber paper or chromatography paper. Alternatively, the surface to be tested itself will be the sample substrate. A conversion reagent is then applied to the sample substrate. The conversion reagent is preferably an organic amine, aromatic amine, aliphatic amine, nitroso compound, an amine containing polymers or combinations thereof. Optionally, the conversion reagent includes a catalyst dissolved in a solvent, such as a volatile organic solvent. In addition, the organic amine and/or catalyst is preferably chemically modified to increase its solubility in preferred solvents, or chosen in part by reference to its solubility. The organic amine may also be chemically modified to decrease harmful (e.g., carcinogenic) effects, such as by incorporating the reactive functional groups into higher molecular weight polymers or macromolecules or into cage structures or by increasing the steric hindrance around the reactive group to reduce bioavailability and environmental mobility. Strategic chemical substitution on the aromatic ring may also serve to promote bio-safety, such as with ester groups to make amino benzoates and diamino benzoates. The organic amine may also be chemically modified to affect other benefits, such as solubility, reactivity, sensitivity, and reaction time. For example, the amine may be a functionalized aniline or dianiline. The amine functionality may also be incorporated in or attached to dendrimers or polymer structures. This increases the number of reactive sites per molecule.

The conversion reagent may be applied to the sampling substrate by various means, such as using an airbrush to create a thin coating of the reagent on the substrate. Other means of applying the conversion reagent include use of an aerosol container, a pumping mechanism, drop-coating the reagent onto the substrate, or by other means. In one embodiment, the conversion reagent is contained in microcapsules, which are applied to the sample substrate by breakage of the microcapsules. The sample and or sampling substrate may also be submerged into the conversion reagent as will be discussed in more detail below. In another embodiment, the conversion reagent is applied to the sampling substrate prior to collection of the sample. Optionally, the conversion reagent may be embedded into the sampling substrate prior to collecting the sample, such as by pre-impregnating the sampling substrate with the conversion reagent or by coating of the sample substrate with microcapsules containing the conversion reagent.

After application of the conversion reagent, the sample substrate is preferably observed under white light. The appearance of a distinct color change observable under white light may indicate the presence of some chemical analogues of peroxide-based explosives.

A test or detection reagent is next applied to the sample or sampling substrate. The detection reagent contains a luminescent compound dissolved in a solvent, such as a volatile organic solvent. Preferably, the luminescent compound is selected from luminescent polyacetylenes, polyvinylenes, polyphenylenes, polyfluorenes, polyp-phenyleneethynylenes), polyp-phenylenevinylenes), poly(fluorenylvinylenes), poly(fluorenylethynylenes), poly(fluoreneylphenylenes), polycarbazoles, carbazole-containing polymers and monomers, biphenyls, aromatic hydrocarbons, aromatic heterocycles, conjugated organic polymers, inorganic polymers, cationic fluorophores, rhodamines, rhodamine B, rhodamine 6G, rhodamine 110, sulfonated rhodamines, coumarins, and 3,3'-[(9,9-dihexyl-9H-fluorene-2,7-diyl)di-2,1-ethenediyl]bis[9-ethyl-9H-carbazole] and combinations thereof. Preferably, the solvent is selected to maximize mixing of the test reagent and any explosive residue present, and is selected from the group consisting of alcohols, diethyl ether, tetrahydrofuran, acetone, pentane(s), hexane(s), toluene, xylene(s), water, ethyl acetate, acetonitrile, dimethyl sulfoxide, N-Methyl-2-pyrrolidone, dimethylformamide and mixtures thereof. Optionally, the luminescent compound may be chemically modified to increase its solubility in preferred solvents or to reduce its hazardous properties.

The detection reagent can further include an aminoaromatic aldeyhde selected from the group consisting of p-(dimethylamino) benzaldehyde and p-(dimethylamino) cinnamaldehyde. The aminoaromatic aldeyhde will react with any urea nitrate present on the sample substrate to produce a product that will create a color change or a change in luminescence that may be detected visually.

Like the conversion reagent, the detection reagent can be applied to the sampling substrate by various means, such as by using an airbrush an aerosol container, a pumping mechanism, by drop-coating, or by other means, such as by breaking of microcapsules containing the detection reagent, to create a coating of the detection reagent on the substrate.

After application of the detection reagent, the sample substrate is then exposed to a wavelength of light capable of exciting luminescence from the luminescent material, such as light from a UV lamp, UV-light emitting diodes, or UV-emitting cold cathodes. In some instances, UV-light is a necessary catalyst to initiate the reaction, especially for peroxide and inorganic nitrate based explosives. Continued exposure to UV-light may also increase the rate of reaction. The wavelength of light may also be chosen in reference to its ability to catalyze the reaction between the explosives and the conversion reagent, i.e., chosen in reference to the absorbance of the reactants. In one embodiment of the invention, two UV-light sources are utilized either simultaneously or in parallel, if the wavelength needed to catalyze the reaction is different from the wavelength needed to excite luminescence. Detection of an explosive is confirmed by observing the change in luminescence, such as a. quenching of luminescence, or the process of quenching over time. Detection may also be observed if some products of the reaction between some explosives and the conversion reagent are UV-absorbing materials, which appear dark against the luminescent background. Highly oxidizing explosives such as nitroaromatics, nitramines, and nitrate esters are often observable immediately, or upon solvent evaporation. In some cases, the degree of luminescence quenching for all explosives, especially those that undergo a chemical reaction (e.g., peroxides) may increase upon allowing the signal to develop over time. The quenching may be observed visually if a compound that displays luminescence in the visible spectrum is used. The quenching may also be observed instrumentally with the use of a visible or ultraviolet camera, a fluorimeter (e.g., fluorescence spectrophotometer), a computer, or by other means. If discrimination between peroxide-based explosives and chemical analogues of organic peroxide-based explosives is desired, a secondary light source of white light is utilized, as there are some cases in which the chemical analogues of peroxide-based explosives produce colored spots on the sampling substrate after reaction with the detection and conversion reagents.

In other embodiments of the invention, the order of addition may be reversed such that the substrate is exposed to the detection reagent prior to being exposed to the conversion reagent. In accordance with various embodiments of the present invention, the detection reagent and the conversion reagent may be present in the same mixture and applied to the sample and/or sampling substrate simultaneously, or the two reagents may be stored separately but applied simultaneously.

Heat may be applied to the sampling substrate after the application of the test reagents. This serves multiple purposes, one of which is to speed the chemical reactions taking place, and also to speed the evaporation of solvent so that observation of the luminescence and luminescence quenching may be performed more rapidly. Heat further serves to increase the rate of interaction between the luminescent sensing material and the compounds which interact with the luminescent material to effect a change in fluorescence, such as quenching. Heat may help partially vaporize the quenching compounds which will improve their ability to diffuse into and subsequently condense into the sensing material. Quenching may then be observed once there is sufficient mixing of explosive analyte and sensor material to affect quenching.

An additional application of this method to peroxide explosive detection would be through a chemical assay approach. Rather than exposing a substrate to possible explosives, an aliquot of the bulk explosives is added to a solution of the conversion reagent. After a specified amount of reaction time, this assay is spotted onto a substrate, the detection reagent is then applied and then the sampling substrate exposed to UV light so that quenching may be observed. Alternatively, the sample may be added to a solution containing both the detection reagent and conversion reagent prior to spotting on a sample substrate and observing a change in luminescence under UV light.

Based on the above discussion, it should be understood that a one or two-step approach may be implemented to effect the detection of peroxide-based explosives, and other highly oxidizing species. With the two-step approach, a sample is collected using the sampling substrate, or a surface to be tested is selected. The conversion reagent is applied to the contaminated surface and reacts with any peroxide, nitrate, chlorate, or bromate present to produce a product(s), such as nitroaromatics. The detection reagent is then applied onto the surface and quenching occurs at all locations where the reaction product(s) had formed. The resulting quenching is visually observed with the substrate being illuminated under UV light, and indicates the presence of explosives. The observation of colored products under white light distinguishes potential interference from chemical analogues of peroxide-based explosives. In contrast, with the one-step approach, the conversion and detection reagents are applied to the contaminated surface simultaneously, either from a combined solution or from two separate solutions applied simultaneously or substantially simultaneously.

It is possible that a nitrosoaromatic intermediate will be a partial product in the reaction between an aromatic amine in the conversion reagent and peroxide or other explosives present on the sample substrate. Therefore, in some embodiments of the invention, the nitrosoaromatic intermediate is utilized in lieu of aromatic amines to effect more efficient nitroaromatic production.

Advantageously, all embodiments of the invention involve the use of fluorescent compounds whose luminescence is quenched in the presence of nitroaromatic compounds and other strong electron-accepting molecules, such as high explosives (e.g., nitroaromatics, nitramines, and nitrate esters). Therefore, this invention may be used for concurrent or subsequent detection of both peroxide-based explosives and other classes of high explosives (e.g., nitroaromatics, nitramines, nitrate esters, inorganic nitrates, chlorates, bromates, and powders). Detection of the high explosives mentioned occurs whenever the detection reagent (containing a fluorophore) is applied to the substrate as discussed in the embodiments above, as high explosives are able to quench the fluorescence of the fluorophore. It has also been discovered that the addition of the conversion reagent dramatically increases the detection sensitivity of weak quenchers, such as inorganic nitrate explosives and smokeless and black powders. The conversion reagent may also serve to enhance the fluorescence intensity of the luminophore, thereby increasing signal to noise of high explosives, nitrates and powders, and increasing detection sensitivity. While many fluorophores themselves do not detect these classes of explosives, or do so only weakly, solutions containing both fluorophores and a conversion reagent, such as an aromatic amine, detect these explosives at trace levels. It is hypothesized that the increased sensitivity in detection of nitroaromatics, nitramines and nitrate esters resulting from addition of the conversion reagent to the test reagent is the result of either a brightening of the fluorescent background, and hence higher signal to noise in the quenching, or from a photophysical oxidation of the conversion reagent by the explosives, resulting in an increased quenching efficiency. Thus, fluorophores and conversion reagents work in conjunction to simultaneously detect a wide range of explosive classes, including nitroaromatics, nitramines, nitrate-esters, inorganic nitrates, chlorate-, perchlorate-, bromate-, peroxides, and smokeless and black powders.

Advantageously, the detection method of the present invention can be utilized to detect multiple classes of explosives, (e.g., nitroaromatics, nitramines, nitrate-esters, inorganic nitrates, chlorate-, perchlorate-, bromate-, peroxides, and smokeless and black powders) in tandem or in situ. In one method, the detection reagent is applied to the substrate first, allowing for the detection of high explosives before adding the conversion reagent to the same substrate to effect the detection of other explosives, including the less-efficient quenchers and reactive species. This method may be improved using a second application of the detection reagent once the conversion reagent has been applied to promote efficient mixing of chemicals. This method is advantageous in that it allows a user to distinguish high explosives from the other classes of explosives.

For users who desire a more rapid detection and are not concerned with differentiating different types of explosives, the detection reagent and conversion reagent can be combined into a single solution for the one-step detection of multiple classes of explosives. Alternatively, if the combination of the two reagents in solution caused chemical compatibility issues, the conversion reagent can be applied prior to, the detection reagent on the same substrate. Alternatively, the two reagents can be stored separately but applied simultaneously in order to avoid chemical incompatibility issues.

In addition to the improvements in nitrogen-based explosives detection due to the conversion reagent, the method of the present invention preferably includes the step of applying a phase transfer reagent to the sample substrate. The nitrate anion, $NO_3^-$, has been found to interact with fluorophores in aqueous solution, resulting in luminescence quenching. It may also be possible for nitrate to alter or quench the luminescence of luminophores, such as conjugated organic polymers, in organic solvents. The obstacle to luminescence alteration, which may be a quenching, brightening or wavelength shift of luminescence, by inorganic nitrates is often the lack of strong interactions between nitrate and the luminophore, which may result from the poor solubility of the inorganic nitrate in organic solvents as well as electrostatic repulsion between the anionic nitrate and the typically electron-rich luminophore. The use of the phase transfer reagent in the present method increases the interaction between nitrate and luminophore species by increasing the solubility of inorganic nitrates in organic solvent systems and reducing or eliminating electrostatic repulsion between the nitrate ion and luminophore. Such increased interaction results in luminescence alteration and the concomitant ability to detect inorganic nitrates through the observance of the resultant change in luminescence.

The changes in emission of the luminophores can be caused by a number of mechanisms, such as (1) luminescence quenching through electron-transfer from the luminophore to the nitrate anion; (2) ion-pairing between the nitrate anion and the luminophore, particularly where cationic luminophores are used, that results in either quenching of the luminophore or a wavelength shift in its luminescence; and (3) a chemical reaction that either forms a new compound with a disparate emission wavelength or that quenches the luminescence of the original luminophore.

The classes of phase transfer reagents used in this invention may include the following: (1) cationic ammonium compounds, such as tetraalkylammonium salts and cationic ammonium surfactants, (2) nonionic polyethers, such as linear surfactants and cyclic crown ethers, and (3) polyaromatic, cationic luminophores, such as organic dyes. In the latter case, the cationic luminophore itself acts as the phase transfer reagent. Examples of cationic ammonium compounds which may act as phase transfer reagents are tetramethylammonium bromide, tetraethylammonium bromide, tetrabutylammonium bromide, octyltrimethylammonium chloride, benzyldimethyldecylammonium chloride, and hexadecyltrimethylammonium bromide. The chloride salt of the anthracene-based cation resulting from quaternization of 1-N-butylimidazole using 9,10-bis(chloromethyl)anthracene may also be used. Ammonium salts containing alkyl substituents of sizes intermediate or larger than those listed may also be used, as well as substituents containing aromatic groups such as benzyl or phenyl. Analogues of these salts comprising alternate anions such as iodide, sulfate, and other anions may also be employed. The solubilizing capabilities of the shorter-chain ammonium salts stem from their ability to draw the nitrate counterions through electrostatic attraction into the organic solvent systems in which the ammonium cations are freely soluble. The longer-chain ammonium salts act as surfactants, forming micellar species whose hydrophilic sections attract the nitrate anion and whose hydrophobic sections draw the entire molecule and nitrate anion into the organic systems. Once in the organic systems, the electrostatic attraction between the cationic phase-transfer reagents and the electron-rich luminophores also brings the nitrate anions, which also are electrostatically attracted to the cationic phase-transfer reagents, into closer contact with the luminophores, resulting in luminescence alteration.

Examples of nonionic polyether reagents which may act as phase transfer reagents are 1,4,7,10,13,16-hexaoxacyclooctadecane (commonly called 18-crown-6) and oligo- and polyethylene glycols (PEGs) and their derivatives, including triethylene glycol, tetraethylene glycol, pentaethylene glycol, and their respective mono- and dialkyl ethers. Polyethylene glycols of varying molecular weights, such as PEG 200, PEG 300, and PEG 400, and their alkyl ethers may also be used, as well as crown ethers and nitrogen-containing aza-crown compounds of varying, sizes and complexing abilities. The polyether reagents solubilize the inorganic nitrates by coordinating their respective cations, forming, for example, organic soluble $[K(18\text{-crown-}6)]^+$ or $[Na(18\text{-crown-}6)]^+$ cationic complexes. The solubilization of the inorganic cations in the organic solvent system electrostatically attracts the nitrate anion, which may then interact with the luminophore to effect an alteration in luminescence. In these nonionic polyether systems, the nitrate anion is made especially available to the luminophores because it is not closely associated with the polyether-complexed cation.

Examples of cationic luminophores which may act as both the luminophore and the phase transfer reagent are rhodamine B, rhodamine 6G, and rhodamine 110. These dyes are each known by several alternative names, such as basic violet 10, brilliant pink B, tetraethylrhodamine (rhodamine B); basic red 1, basic rhodaminic yellow (rhodamine 6G); and o-(6-amino-imino-3H-xanthe-9-yl)benzoic acid chloride (rhodamine 110 chloride). Other rhodamine and cationic luminophores are also successful utilized by this method. These cationic luminophores act as phase-transfer reagents by electrostatically drawing the inorganic nitrates into the organic solvents. The favorable electrostatic interaction between the anionic nitrate and the cationic luminophore results in luminescence alteration. In a preferred method of the present invention, the phase transfer reagent is selected from cationic ammonium compounds, nonionic polyethers, and cationic luminophores, wherein said cationic ammonium compounds are selected from the group consisting of tetralkylammonium salts, said nonionic polyethers are selected from the group consisting of polyethylene glycols, cyclic polyethers, crown ethers, aza-crown compounds, and said cationic luminophores are selected from the group consisting of rhodamines, rhodamine B, rhodamine 6G, rhodamine 110, sulfonated rhodamines, and coumarins.

The compounds p-(dimethylamino)benzaldehyde (DMAB) and p-(dimethylamino)cinnamaldehyde (DMAC), or other aminoaromatic aldehydes, hereinafter referred to as colorimetric reagents, may be used in combination with each of the three classes of phase transfer reagents and luminophores previously described to specifically distinguish uronium nitrate from other nitrate species via a chemical reaction that yields a colored compound, e.g., a yellow compound, when using DMAB, or a red compound, when using DMAC. The colorimetric reagent may be applied before, after, or simultaneously with the luminophore and phase transfer reagent. In this way, the presence of uronium nitrate may be distinguished from the presence of the other nitrates. For example, a solution containing a cationic luminophore and DMAC may be applied to a surface containing nitrates. A distinct fluorimetric signal would be observed to identify the presence of nitrates and the appearance of a red-colored product would confirm the identity of the nitrate as urea nitrate. Furthermore, the discrimination between explosives can be performed by observing the change in the luminescence signal, whereby the shift in luminescence caused by a particular nitrate is distinct from that caused by another. This latter method of discrimination between explosives based on the difference in the alteration of the luminescence signal may be performed both with and without the addition of the colorimetric reagent. Other colorimetric detection techniques may be used in conjunction with this luminescent technique to confirm the presence of and/or distinguish the identity of different nitrate based compounds.

A method of applying the three types of phase transfer reagents will now be discussed in more detail. First, a test reagent is prepared by dissolving the luminophore or luminescent compound of choice in a solution containing one or a combination of the phase transfer reagents described above. Optionally, a colorimetric reagent may be added. When the luminophore itself is the phase-transfer reagent, it may be used alone or in combination with any of the other phase-transfer and colorimetric reagents previously discussed. The solvent system may contain a mixture of various organic solvents and water. The resulting test reagent containing the luminophore and phase transfer reagent(s) is applied to the sample substrate on which inorganic nitrates have been deposited or may have been deposited. Application may be achieved with an airbrush or nebulizer attached to an aerosol can or by other means, such as the breakage of microcapsules containing the various reagents and solvents. After application of the luminophore/phase-transfer solution, UV light is used to excite the luminophore. The observation of a distinct change in luminescence, such as dark spots, bright spots, or colored spots against the luminescing background of the illuminated sample substrate surface indicates the presence of inorganic nitrates. If a colorimetric reagent is used, the detection of nitrates using luminescence alteration under UV light may be followed by viewing of the surface under white light to confirm the identity of the nitrate as uronium nitrate if a colored product appears, e.g., if a yellow (from DMAB) or red (from DMAC) color is observed. This color change is observable under white light and under UV light. Thus, if no color is observed under white light for a sample that displays luminescence alteration under ultraviolet light, the nitrate present is most likely not uronium nitrate.

As previously noted, the mechanism for formation of a quenching agent in the present invention is thought to rely on photo-oxidation of the conversion reagent. UV-light is an efficient promoter of the reaction to occur. The UV light needed to promote the reaction, however, need not be the same wavelength, or wavelength range, as the UV light needed to excite fluorescence of the test reagent. Therefore, two wavelengths, or wavelength ranges, may be used to effect detection. One may promote the conversion of the conversion reagent in the presence of explosives (peroxide, inorganic nitrate, chlorate, bromate, perchlorate, and powders) while the other may be used to excite fluorescence of the fluorophore and observe quenching. In one embodiment of the present invention, a two-step UV radiation approach is utilized to reduce false alarms. More specifically, after application of the conversion reagent, with or without the phase transfer reagent and/or test reagent, a first wavelength of light selected to catalyze the reaction between the conversion reagent and explosives is applied. The application of the second wavelength of light may be performed separately, either in time or space, to view quenching and determine whether traces of explosives are present.

This method of detecting inorganic nitrates may be used in conjunction with luminescent techniques to detect nitrogen-based high explosives, such as nitroaromatics, nitramines, and nitrate esters. Thus, application of the luminophore/phase-transfer solutions to surfaces containing high explosives results in the detection of the high explosives via their luminescence alteration of the luminophore. High explosives and inorganic nitrates present on the same surface are detected simultaneously using the luminophore/phase-transfer solutions, which may be used in conjunction with the colorimetric reagent.

Alternatively, high explosives and inorganic nitrates may be detected sequentially using a combination of the luminophore/phase-transfer, luminophore-only, phase-transfer-only, and solvent-only solutions. Thus, the invention provides for the two-step detection of high explosives and inorganic nitrates in conjunction with one another. In one sequential detection method, a luminophore-only solution is first applied, which results in detection of only the high explosives. A subsequent application of the luminophore/phase-transfer or phase-transfer-only solutions results in additional detection of the inorganic nitrates. The reverse order of detection is also successful, whereby inorganic nitrates and high explosives are first detected simultaneously using the luminophore/phase-transfer solutions, and the detection of the high explosives is improved by next applying luminophore-only solutions. Application of luminophore/phase-transfer solutions followed by a solvent-only system (no phase transfer reagent and no luminophore) results in simultaneous detection of inorganic nitrates and high explosives followed by improved high explosive detection. All the detection methods just described proceed at ambient temperatures. Application of heat aids in mixing of the systems and subsequent drying, resulting in greater sensitivity of detection and faster detection times. The identification of specific nitrates may be confirmed by using a colorimetric reagent in any of the solutions applied at any step in the preceding procedures as well, or by observing distinct luminescent signals that are specific to individual nitrates.

Detection of inorganic nitrates may be aided by the addition of zinc dust at any point during the detection procedure employing phase-transfer reagents and luminophores. Zinc reduces nitrate to nitrite, which more strongly changes or quenches the emission of the luminophores. The zinc dust may be suspended in a solvent such as dimethyl sulfoxide and applied via aerosol can, or applied by other means. Zinc may also be preimpregnated into sampling substrates so it is present before a sample suspected of containing nitrates is collected.

Advantageously, the present invention sets forth methods whereby both trace peroxide-based explosives and trace nitrogen-based explosives may be detected without the utilization of strong acids or repeated wet-chemistry style sampling steps. The present invention also sets forth methods which may be utilized in the field to simultaneously detect a plurality of explosives without the need for cumbersome detection equipment. The application of reagents may be performed in series to help distinguish which general classes of explosives are present. For example, application of a test regent containing a fluorophore may first be applied to detect nitroaromatic, nitramine, and nitrate ester based explosives. A subsequent application of the phase transfer reagent may then be applied to test for inorganic nitrate based explosives. A subsequent application of a conversion reagent may then be applied to test for peroxide based explosives, as well as chlorates, perchlorates, bromates, and powders. Although described with reference to preferred embodiments of the invention, it should be readily understood that various changes and/or modifications can be made to the invention without departing from the spirit thereof. For example, when referring to the application of reagents, it should be understood that the application should be considered to incorporate sample substrates which have been pre-treated with the reagents prior to actual sampling of a surface to be analyzed. In general, the invention is only intended to be limited by the scope of the following claims.

We claim:

1. A method for detecting one or more trace explosives comprising:
    applying at least one of a conversion reagent that oxidizes in the presence of peroxide explosives and in the presence of inorganic nitrate explosives to produce a quenching agent and a phase transfer reagent that increases solubility of inorganic nitrates in an organic solvent to a sample substrate that may include explosive residue;
    applying a test reagent to the sample substrate, wherein said test reagent contains an organic solvent and a luminescent compound which, upon excitation, undergoes a change in luminescence in the presence of any one or more of nitroaromatic-, nitramine-, nitrate ester-, inorganic nitrate-, chlorate-, perchlorate-, bromate-, peroxide-, smokeless powder- or black powder-based explosives;
    exciting the luminescent compound to cause luminescence; and
    determining whether traces of any one or more of the explosives are present on the sample substrate based on a quenching, brightening or a shift in wavelength of the luminescence.

2. The method of claim 1, wherein the step of applying at least one of the conversion reagent and the phase transfer reagent includes applying both the conversion reagent and the phase transfer reagent.

3. The method of claim 1, further comprising: determining the presence of the one or more of the explosives on the sample substrate based on a change in color resulting from the presence of the one or more of the explosives.

4. The method of claim 3, further comprising: applying a colorimetric reagent to the sample substrate.

5. The method of claim 4, wherein the colorimetric reagent is an aminoaromatic aldehyde, the step of exiting the luminescent compound includes exposing the sample substrate to ultraviolet light, and determining the presence of the one or more of the explosives includes the step of exposing the sample surface to white light, wherein both the quenching of the luminescence under ultraviolet light and the presence of color under white light confirms the presence of urea nitrate.

6. The method of claim 1, wherein the step of applying at least one of the conversion reagent and the phase transfer reagent includes applying the conversion reagent, the method further comprising: exposing the sample substrate to ultraviolet light having a first wavelength selected to catalyze the oxidation of the conversion reagent in the presence of peroxide explosives and in the presence of inorganic nitrate explosives.

7. The method of claim 6, wherein exciting the luminescent compound to cause luminescence is practiced by exposing the sample substrate to ultraviolet light having a second wavelength, after the step of exposing the sample substrate to ultraviolet light having the first wavelength, to initiate a photochemical reaction and the step of determining whether traces of any one or more of the explosives are present on the sample substrate is practiced following exposing the sample substrate.

8. The method of claim 1, wherein said luminescent compounds are chosen from the group consisting of luminescent polyacetylenes, polyvinylenes, polyphenylenes, polyfluorenes, poly(p-phenyleneethynylenes), poly(p-phenylenevinylenes), poly(fluorenylvinylenes), poly(fluorenylethynylenes), poly(fluoreneylphenylenes), polycarbazoles, carbazole-containing polymers and monomers, biphenyls, aromatic hydrocarbons, aromatic heterocycles, conjugated organic polymers, inorganic polymers, and 3,3'-[(9,9-dihexyl-9H-fluorene-2,7-diyl)di-2,1-ethenediyl]bis [9-ethyl-9H-carbazole] and combinations thereof.

9. The method of claim 1, wherein the step of applying at least one of the conversion reagent and the phase transfer reagent includes applying the conversion reagent, wherein said conversion reagent is selected from the group consisting of organic amines, aromatic amines, aliphatic amines, nitroso compounds, amine containing polymers and combinations thereof.

10. The method of claim 1, wherein the step of applying at least one of the conversion reagent and the phase transfer reagent includes applying the phase transfer reagent to alter electrostatic repulsion forces, wherein said phase transfer reagent is selected from the groups consisting of cationic ammonium compounds, nonionic polyethers and combinations thereof, wherein said cationic ammonium compounds are selected from the group consisting of tetralkylammonium salts, and said nonionic polyethers are selected from the group consisting of polyethylene glycols, cyclic polyethers, crown ethers, and aza-crown compounds.

11. The method of claim 1, further comprising: an initial step of collecting a sample from a surface to be tested utilizing the sample substrate.

12. The method of claim 1, wherein determining a quenching, brightening, or a shift in wavelength of luminescence is performed using a fluorimeter, camera, computer, or visual inspection.

13. The method of claim 1, wherein the step of applying at least one of the conversion reagent and the phase transfer reagent includes applying the conversion reagent, and the method further comprises applying a catalyst to aid in the reaction of said explosives with said conversion reagent to affect said quenching of the luminescence.

14. The method of claim 1, further comprising:
applying an aminoaromatic aldeyhde that reacts with urea nitrate to produce a product, wherein said aminoaromatic aldehyde is selected from the group consisting of p-(dimethylamino)benzaldehyde and p-(dimethylamino)cinnamaldehyde; and
determining the presence of urea nitrate on the sample substrate based on a change in color resulting from the presence of said product or a change in luminescence resulting from the presence of said product.

15. The method of claim 1, wherein one or more of said conversion reagent, said phase transfer reagent and said test reagent are applied to the sample substrate in the form of microcapsules.

16. The method of claim 1, further comprising: applying zinc dust to the sample substrate to aid in the detection of inorganic nitrate explosives.

17. The method of claim 1, wherein the at least one of the conversion reagent and phase transfer reagent is applied to the sample substrate simultaneously with the test reagent.

18. The method of claim 1, wherein the at least one of the conversion reagent and phase transfer reagent is applied to the sample substrate step-wise with the test reagent.

19. The method of claim 1, wherein at least one of the conversion reagent and luminescent compound has been modified to decrease toxicity.

20. The method of claim 1, wherein the step of applying the test reagent is completed before the step of applying the at least one of a conversion reagent and a phase transfer reagent; the step of applying the at least one of a conversion reagent and a phase transfer reagent comprises applying step-wise a conversion reagent and a phase transfer reagent; and the step of determining whether traces of any one or more of the explosives are present is conducted after the application of each of the conversion reagent and phase transfer reagent so as to enable the step-wise detection of different types of explosives.

* * * * *